(12) United States Patent
Zaragoza Doerwald et al.

(10) Patent No.: US 9,663,436 B1
(45) Date of Patent: May 30, 2017

(54) METHOD FOR PREPARATION OF 4-ALKOXY-1,1,1-TRIFLUOROBUT-3-EN-2-ONES FROM 1,1,1-TRIFLUOROACETONE

(71) Applicant: Lonza Ltd, Visp (CH)

(72) Inventors: Florencio Zaragoza Doerwald, Visp (CH); Christoph Taeschler, Visp (CH)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 15/309,957

(22) PCT Filed: Jun. 24, 2015

(86) PCT No.: PCT/EP2015/064241
§ 371 (c)(1),
(2) Date: Nov. 9, 2016

(87) PCT Pub. No.: WO2015/197682
PCT Pub. Date: Dec. 30, 2015

Related U.S. Application Data

(60) Provisional application No. 62/017,385, filed on Jun. 26, 2014.

(30) Foreign Application Priority Data

Jun. 26, 2014 (EP) .................................... 14174009
Jul. 11, 2014 (EP) .................................... 14176705

(51) Int. Cl.
*C07C 45/70* (2006.01)

(52) U.S. Cl.
CPC .................................. *C07C 45/70* (2013.01)

(58) Field of Classification Search
CPC ....................................................... C07C 45/70
USPC ............................................................ 568/388
See application file for complete search history.

(56) References Cited

U.S. PATENT DOCUMENTS

2012/0101305 A1   4/2012   Braun et al.
2013/0079377 A1   3/2013   Frank et al.
2014/0051892 A1   2/2014   Braun et al.

FOREIGN PATENT DOCUMENTS

| DE | 2429674 | 1/1976 |
| EP | 0051209 | 5/1982 |
| WO | WO00/39094 | 7/2000 |
| WO | WO2004/078729 | 9/2004 |
| WO | WO2005/026149 | 3/2005 |
| WO | WO2006/059103 | 6/2006 |
| WO | WO2008/013414 | 1/2008 |
| WO | WO2012/061926 | 5/2012 |

OTHER PUBLICATIONS

Okada, et al., "A Simple and Convenient Synthetic Method for α-Trifluoromethylpyridines", Heterocycles, vol. 46, 1997, pp. 129-132.
International Search Report and Written Opinion for PCT/EP2015/064241, Dated Aug. 27, 2015.

*Primary Examiner* — Sikarl Witherspoon
(74) *Attorney, Agent, or Firm* — Dority & Manning, P.A.

(57) ABSTRACT

The invention discloses a method for the preparation of 4-alkoxy-1,1,1-trifluorobut-3-en-2-ones from 1,1,1-trifluoroacetone.

9 Claims, No Drawings

METHOD FOR PREPARATION OF 4-ALKOXY-1,1,1-TRIFLUOROBUT-3-EN-2-ONES FROM 1,1,1-TRIFLUOROACETONE

RELATED APPLICATIONS

This application is the national stage entry of International Patent Application No. PCT/EP2015/064241 having a filing date of Jun. 24, 2015, which claims the filing benefit of European Patent Application No. 14174009.2, having a filing date of Jun. 26, 2014, U.S. Provisional Patent Application No. 62/017,385, having a filing date of Jun. 26, 2014, and European Patent Application No. 14176705.3, having a filing date of Jul. 11, 2014, all of which are incorporated herein by reference in their entirety.

The invention discloses a method for the preparation of 4-alkoxy-1,1,1-trifluorobut-3-en-2-ones from 1,1,1-trifluoroacetone.

BACKGROUND OF THE INVENTION

4-Alkoxy and 4-aryloxy-1,1,1-trifluorobut-3-en-2-ones of formula (I) are important synthetic intermediates for the preparation of fluorinated heterocycles.

2-Trifluoromethylpyridines and 6-trifluoromethylpyridine-3-carboxylic acid derivatives are intermediates for the preparation of biologically active compounds. For instance, WO 00/39094 A1 discloses trifluoromethylpyridine as herbicides, WO 2006/059103 A2 discloses trifluoromethylpyridines as intermediates in the production of pharmaceutical, chemical and agro-chemical products, WO 2008/013414 A1 discloses trifluoromethylpyridines as vanilloid receptor antagonists and WO 2012/061926 A1 describes trifluoromethylpyridines as calcium channel blockers.

WO 2005/026149 A, DE 24 29 674 A and EP 51 209 A disclose certain precursors used in instant invention.

The common route for the preparation of 6-trifluoromethylpyridine-3-carboxylic acid derivatives was first reported by Okada et al., Heterocycles 1997, 46, 129-132, and has only been slightly modified by others. The common synthetic strategies are summarized in Scheme 1:

This route has disadvantages for the large scale production of 6-trifluoromethylpyridine-3-carboxylic acid derivatives, because ethylvinylether is highly flammable and therefore difficult to handle, and because the trifluoroacetylated enolether and the trifluoroacetylated enamine intermediates are unstable and cannot be stored for a longer time. Moreover, most vinyl ethers are mutagenic.

US 20130079377 describes the use and preparation from vinyl ethers of 4-alkoxy-1,1,1-trifluorobut-3-en-2-ones for the synthesis of novel vanilloid receptor ligands.

US 20120101305 discloses the preparation of 4-alkoxy-1,1,1-trifluorobut-3-en-2-ones from vinyl ethers and trifluoroacetyl chloride.

US 20140051892 A1 discloses a method for the preparation of 4-ethoxy-1,1,1-trifluorobut-3-en-2-one by reacting trifluoroacetyl chloride with ethyl vinyl ether, followed by thermolysis of the resulting chlorinated intermediate. A disadvantage of this method is the formation of hydrogen chloride, which is corrosive and could lead to a product of low storability.

WO 2004/078729 A1 discloses the preparation of compound of formula (Xa) from inter alia 4-alkoxy-1,1,1-trifluorobut-3-en-2-ones;

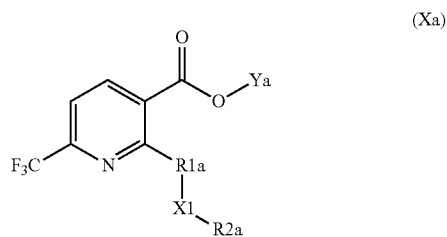

(Xa)

and discloses on page 18 in example P2 the use of 4-ethoxy-1,1,1-trifluorobut-3-en-2-one for the preparation of compound of formula (X-1).

Scheme 1

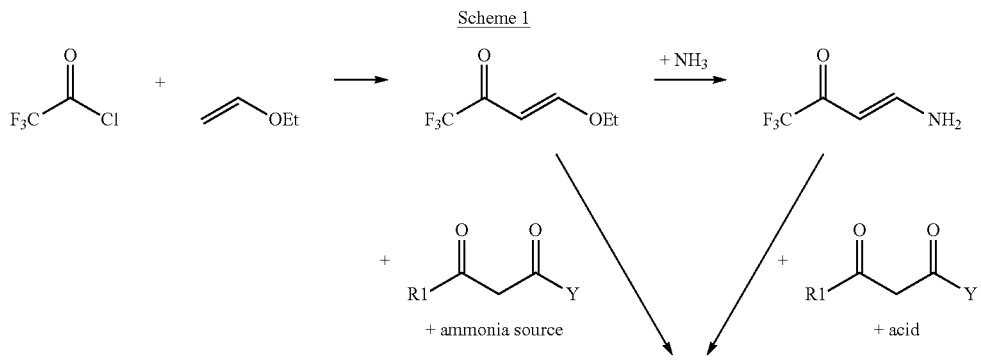

+ ammonia source

+ acid

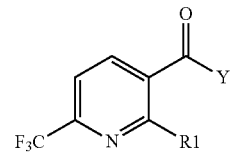

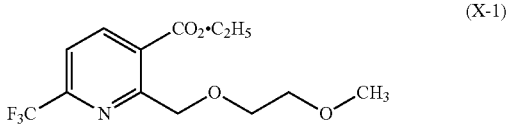

Compound of formula (Xa) and compound of formula (X-1) are intermediates for the preparation of herbicides.

All known routes to 4-alkoxy-1,1,1-trifluorobut-3-en-2-ones are based on the reaction of vinyl ethers with trifluoroacetyl chloride or trifluoroacetic anhydride, whereupon one equivalent of HCl or trifluoroacetic acid are formed as byproducts, that must usually be trapped by addition of a base to prevent the acid-mediated degradation of the product. A further disadvantage of this synthetic strategy for the large scale production of 4-alkoxy-1,1,1-trifluorobut-3-en-2-ones is the high flammability and mutagenicity of vinyl ethers.

There was a need for an improved method for the preparation of 4-alkoxy-1,1,1-trifluorobut-3-en-2-ones. The method should not require the use of the problematic trifluoroacetyl chloride and ethylvinylether. This need was met by the method of instant invention as outlined below.

Compared to prior art, the method of the instant invention offers several advantages: It gives access to 4-alkoxy-1,1,1-trifluorobut-3-en-2-ones without the formation of hydrogen chloride. Only acetic acid, ethyl acetate, and ethyl formate are formed as byproducts, allowing the use of non-HCl-resistant reactors. Importantly, no problematic vinyl ethers are required. Moreover, the method of the present invention only comprises one synthetic step, and is therefore less costly than the two-step procedure disclosed in US 20140051892 A1.

In the following text, if not otherwise stated,
ambient pressure usually 1 bar, depending on the weather;
halogen means F, Cl, Br or I, preferably Cl, Br or I;
alkyl means a linear or branched alkyl, examples of alkyl include methyl, ethyl, n-propyl, isopropyl, n-butyl, sec-butyl, tert-butyl, pentyl, hexyl, heptyl and the like;
cyclic alkyl or cyclo alkyl include cyclo aliphatic, bicyclo aliphatic and tricycle aliphatic residues; examples of "cycloalkyl" include cyclopropyl, cyclobutyl, cyclopentyl, cyclohexyl, cycloheptyl, norbornyl and adamantyl;
alkoxy means alkyl-O, i.e. the radical obtained by removal of the oxygen-bound hydrogen from an aliphatic alcohol;
(alkoxy)alkoxy refers to alkoxy groups, in which the alkyl group is substituted with one additional alkoxy group; examples of (alkoxy)alkoxy include methoxymethoxy with formula MeO—CH$_2$—O—, 2-(methoxy)ethoxy with formula MeO—CH$_2$—CH$_2$—O— and 2-(cyclopropylmethoxy)ethoxy with formula (C$_3$H$_5$)CH$_2$—O—CH$_2$—CH$_2$—O—;
Ac acetyl;
tBu tertiary butyl;
cyanuric acid chloride 2,4,6-trichloro-1,3,5-triazine
DBU 1,8-diazabicyclo[5.4.0]undec-7-ene;
DABCO 1,4-diazabicyclo[2.2.2]octane;
DMF N,N-dimethylformamide;
DMA N,N-dimethylacetamide;
DMSO dimethylsulfoxide;
halogen means F, Cl, Br or J, preferably F, Cl or Br;
hemiacetal refers to the adduct of an alcohol, for instance methanol or ethanol, with a ketone or with an aldehyde; a hemiacetal may also result upon the addition of water to an enol ether; for instance, the hemiacetal of methanol with 1,1,1-trifluoroacetone is F$_3$C—C(OH)(OCH$_3$)—CH$_3$;
hexanes mixture of isomeric hexanes;
hydrate refers to the adduct of water with a ketone or with an aldehyde, for instance, the hydrate of 1,1,1-trifluoroacetone is F$_3$C—C(OH)$_2$—CH$_3$;
LDA Lithium diisopropyl amide
NMP N-methyl-2-pyrrolidone;
sulfamic acid HO—SO$_2$—NH$_2$;
Temp Temperature;
TriFA 1,1,1-trifluoroacetone;
THF tetrahydrofuran;
trifluoroacetone 1,1,1-trifluoropropan-2-one;
xylene 1,2-dimethylbenzene, 1,3-dimethylbenzene, 1,4-dimethylbenzene or a mixture thereof.

SUMMARY OF THE INVENTION

Subject of the invention is a method for the preparation of compound of formula (I);

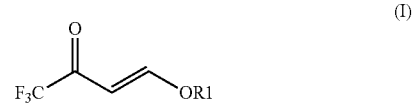

the method comprises step StepS1; step StepS1 comprises a reaction ReacS1; reaction ReacS1 is a reaction of a compound of formula (II) with 1,1,1-trifluoroacetone in the presence of compound of formula (IV);

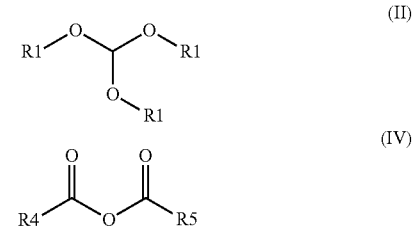

wherein
R1 is C$_{1-4}$ alkyl;
R4 and R5 are identical or different and independently from each other selected from the group consisting of H and C$_{1-4}$ alkyl.

DETAILED DESCRIPTION OF THE INVENTION

Compound of formula (II), 1,1,1-trifluoroacetone and compound of formula (IV) can be mixed for the reaction ReacS1 in any order.

Preferably, R1, is selected from the group consisting of methyl, ethyl, n-propyl, isopropyl and n-butyl;
more preferably, R1 is selected from the group consisting of methyl, ethyl and n-propyl; even more preferably, R1 is methyl or ethyl;
especially, R1 is ethyl.

Preferably, R4 and R5 are identical or different and independently from each other selected from the group consisting of hydrogen and C$_{1-2}$ alkyl;

more preferably, R4 and R5 are identical or different and independently from each other selected from the group consisting of hydrogen and methyl;
even more preferably, R4 and R5 are identical or different and independently from each other hydrogen or methyl; especially, R4 and R5 are methyl.

Preferably, the molar amount of compound (II) is from 1 to 20 times, more preferably from 1 to 10 times, and even more preferably from 1 to 6 times, based on the molar amount of 1,1,1-trifluoroacetone.

Preferably, the molar amount of compound (IV) is from 2 to 60 times, more preferably from 2 to 20 times, and even more preferably from 2 to 10 times, based on the molar amount of 1,1,1-trifluoroacetone.

Reaction ReacS1 can be done in the presence of a catalyst CatS1;
catalyst CatS1 is selected from the group consisting of trifluoroacetic acid, sulfuric acid, $ZnCl_2$, $ZnBr_2$, $ZnI_2$, $BF_3$, $BF_3OEt_2$, $BBr_3$, $BCl_3$, $MgCl_2$, and $CaCl_2$;
preferably, catalyst CatS1 is selected from the group consisting of trifluoroacetic acid, sulfuric acid, $ZnCl_2$, $ZnBr_2$, $ZnI_2$, $BF_3OEt_2$, $BCl_3$, $MgCl_2$, and $CaCl_2$;
more preferably, catalyst CatS1 is selected from the group consisting of trifluoroacetic acid, sulfuric acid, $ZnCl_2$, $BF_3OEt_2$, $MgCl_2$, and $CaCl_2$;
even more preferably, catalyst CatS1 is selected from the group consisting of trifluoroacetic acid, $ZnCl_2$, $BF_3OEt_2$, and $MgCl_2$;
Preferably, the molar amount of catalyst CatS1 is from 0.001 to 2 times, more preferably from 0.005 to 1 times, and even more preferably from 0.01 to 0.5 times, based on the molar amount of 1,1,1-trifluoroacetone.

Preferably, reaction ReacS1 is done at a temperature of from 0° C. to 250° C., more preferably from 20° C. to 200° C., even more preferably from 60° C. to 150° C.

Preferably, reaction ReacS1 is done at a pressure of from ambient pressure to 150 bar, more preferably from ambient pressure to 100 bar, even more preferably from ambient pressure to 70 bar.

Preferably, the reaction time of reaction ReacS1 is from 10 min to 72 h, more preferably from 1 h to 48 h, even more preferably from 2 h to 24 h.

Reaction (ReacS1) can be done in a solvent;
preferably, the solvent is a solvent (SolvS1) and solvent (SolvS1) is selected from the group consisting of ethyl acetate, butyl acetate, dichloromethane, 1,2-dichloroethane, chloroform, acetonitrile, propionitrile, DMF, DMA, DMSO, sulfolane, THF, 2-methyl-THF, 3-methyl-THF, dioxane, 1,2-dimethoxyethane, toluene, benzene, chlorobenzene, nitrobenzene, and mixtures thereof;
more preferably, solvent (SolvS1) is selected from the group consisting of ethyl acetate, butyl acetate, dichloromethane, 1,2-dichloroethane, acetonitrile, propionitrile, DMF, DMA, DMSO, sulfolane, THF, 2-methyl-THF, 3-methyl-THF, dioxane, 1,2-dimethoxyethane, toluene, benzene, chlorobenzene, and mixtures thereof;
even more preferably, solvent (SolvS1) is selected from the group consisting of ethyl acetate, butyl acetate, dichloromethane, 1,2-dichloroethane, acetonitrile, DMF, DMA, sulfolane, dioxane, 1,2-dimethoxyethane, toluene, chlorobenzene, and mixtures thereof;
especially, solvent (SolvS1) is selected from the group consisting of ethyl acetate, butyl acetate, dichloromethane, 1,2-dichloroethane, acetonitrile, DMF, DMA, dioxane, 1,2-dimethoxyethane, toluene, chlorobenzene, and mixtures thereof.

Preferably, the weight of solvent (SolvS1) is from 0.1 to 100 times, more preferably from 1 to 50 times, even more preferably from 1 to 25 times, of the weight of 1,1,1-trifluoroacetone.

After reaction ReacS1, any catalyst CatS1 can be removed by filtration. Compound of formula (I) can be isolated after the reaction ReacS1 by any conventional method, for instance by distillation under reduced pressure or by crystallization. Preferably, any volatile byproduct is distilled off, and the residue is purified or used without further purification.

EXAMPLES

Example 1

A mixture of 1,1,1-trifluoroacetone (0.80 ml, 8.93 mmol), triethylorthoformate (2.23 ml, 13.0 mmol) and acetic anhydride (2.53 ml, 27.0 mmol) was stirred in a closed vial at 140° C. for 16 h.

Analysis of a sample by $^1$H NMR (CDCl$_3$) indicated formation of compound of formula (1) in 65% yield with respect to 1,1,1-trifluoroacetone used.

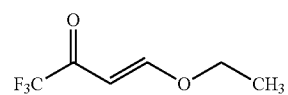

(1)

Examples 2 to 5

Examples 2 to 5 were done in the same way as example 1, with any differences as given in Table 1.

TABLE 1

| Example | HC(OEt)₃ [mmol] | TriFA [mmol] | Ac₂O [mmol] | Molar Ratio (II)/TriFA/ (IV) | Temp [° C.] | Time [h] | yield [%] |
|---|---|---|---|---|---|---|---|
| 2 | 18 | 4.5 | 27 | 4/1/6 | 140 | 10 | 41 |
| 3 | 2.67 | 1.34 | 4 | 2/1/3 | 120 | 12 | 15 |
| 4 | 7.07 | 3.57 | 10.7 | 2/1/3 | 130 | 21 | 37 |
| 5 | 6.68 | 2.23 | 13.4 | 3/1/6 | 130 | 21 | 51 |

Example 6

A mixture of 1,1,1-trifluoroacetone (0.20 ml, 2.2 mmol), trimethylorthoformate (1.0 ml, 9.1 mmol), and acetic anhydride (1.6 ml, 16.9 mmol) was stirred in a closed vial at 140° C. for 16 h. Analysis of a sample by 1H NMR (CDCl$_3$) indicated formation of compound of formula (2) in 78% yield with respect to trifluoroacetone used.

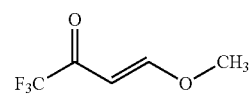

(2)

$^1$H NMR (CDCl$_3$, 400 MHz) delta=3.88 (s, 3H), 5.87 (d, J=12 Hz, 1H), 7.94 (d, J=12 Hz, 1H).
$^{19}$F NMR (CDCl$_3$) delta=78.08 ppm.

The invention claimed is:

1. A method for the preparation of a compound of formula (I);

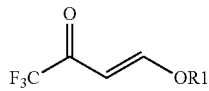

the method comprises step StepS1 comprising a reaction ReacS1;
wherein reaction ReacS1 is a reaction of a compound of formula (II) with 1,1,1-trifluoroacetone in the presence of a compound of formula (IV);

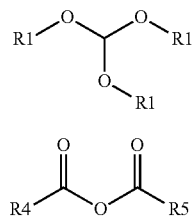

wherein
R1 is $C_{1-4}$ alkyl;
R4 and R5 are identical or different and independently from each other selected from the group consisting of H and $C_{1-4}$ alkyl.

2. The method according to claim 1, wherein
R1 is selected from the group consisting of methyl, ethyl, n-propyl, isopropyl and n-butyl.

3. The method according to claim 1, wherein
R4 and R5 are identical or different and independently from each other selected from the group consisting of hydrogen and $C_{1-2}$ alkyl.

4. The method according to claim 1, wherein
the molar amount of the compound of formula (II) is from 1 to 20 times based on the molar amount of 1,1,1-trifluoroacetone.

5. The method according to claim 1, wherein
the molar amount of the compound of formula (IV) is from 2 to 60 times based on the molar amount of 1,1,1-trifluoroacetone.

6. The method according to claim 1, wherein
reaction ReacS1 is done in the presence of a catalyst CatS1;
wherein catalyst CatS1 is selected from the group consisting of trifluoroacetic acid, sulfuric acid, $ZnCl_2$, $ZnBr_2$, $ZnI_2$, $BF_3$, $BF_3OEt_2$, $BBr_3$, $BCl_3$, $MgCl_2$, and $CaCl_2$.

7. The method according to claim 6, wherein
the molar amount of the catalyst CatS1 is from 0.001 to 2 times based on the molar amount of 1,1,1-trifluoroacetone.

8. The method according to claim 1, wherein
reaction ReacS1 is done at a temperature of from 0° C. to 250° C.

9. The method according to claim 1, wherein
the reaction time of reaction ReacS1 is from 10 min to 72 h.

* * * * *